United States Patent
Sebti et al.

(10) Patent No.: US 10,351,596 B2
(45) Date of Patent: Jul. 16, 2019

(54) γ-AA-PEPTIDE STAT3/DNA INHIBITORS AND METHODS OF USE

(71) Applicant: H. Lee Moffitt Cancer Center and Research Institute, Inc., Tampa, FL (US)

(72) Inventors: Said M. Sebti, Tampa, FL (US); Jianfeng Cai, Tampa, FL (US)

(73) Assignees: H. Lee Moffitt Cancer Center and Research Institute, Inc., Tampa, FL (US); University of South Florida, Tampa, FL (US)

(*) Notice: Subject to any disclaimer, the term of this patent is extended or adjusted under 35 U.S.C. 154(b) by 0 days.

(21) Appl. No.: 15/963,454

(22) Filed: Apr. 26, 2018

(65) Prior Publication Data
US 2018/0244719 A1 Aug. 30, 2018

Related U.S. Application Data

(60) Division of application No. 15/332,402, filed on Oct. 24, 2016, now Pat. No. 10,000,531, which is a continuation of application No. PCT/US2015/027801, filed on Apr. 27, 2015.

(60) Provisional application No. 61/984,179, filed on Apr. 25, 2014.

(51) Int. Cl.
| C07K 7/02 | (2006.01) |
| A61P 35/00 | (2006.01) |
| A61K 38/00 | (2006.01) |
| C07C 237/22 | (2006.01) |

(52) U.S. Cl.
CPC .............. *C07K 7/02* (2013.01); *C07C 237/22* (2013.01)

(58) Field of Classification Search
CPC ................................ C07K 7/02; C07C 237/22
See application file for complete search history.

(56) References Cited

PUBLICATIONS

Niu et al, AApeptides as a New Class of Peptidomimetics to Regulate Protein-Protein Interactions, Chapter 9 from Protein Interactions, 2012, pp. 155-170.*

* cited by examiner

*Primary Examiner* — Karlheinz R. Skowronek
*Assistant Examiner* — Li N Komatsu
(74) *Attorney, Agent, or Firm* — Michele L. Lawson; Smith & Hopen, P.A.

(57) ABSTRACT

STAT3 hyperphosphorylation, dimerization and DNA binding are required for its ability to contribute to malignant transformation. As such, STAT3 has been recognized as a promising target for cancer therapy. Although a number of inhibitors of STAT3-STAT3 dimerization have been reported, molecular ligands that prevent interactions between STAT3 and DNA are very rare. The γ-AApeptide-based one-bead-one-compound (OBOC) combinatorial library was used, and identified γ-AApeptides that can selectively inhibit STAT3/DNA interaction and suppress the expression levels of STAT3 target genes in intact cells. The results not only validate γ-AApeptides as novel inhibitors of STAT3 signaling pathway, but also demonstrate that in addition to the SH2 domain, the DNA binding domain of STAT3 is targetable for the development of new generation of anti-cancer therapeutics. This also validates the approach of OBOC combinatorial library for the identification of ligands targeting traditionally recognized "undruggable targets".

3 Claims, 20 Drawing Sheets
Specification includes a Sequence Listing.

α peptide

γ-AA peptide

Compound 3
MALDI-TOF:
Theo: 1090.73 [M+1]⁺
Found: 1090.60

Compound 4
MALDI-TOF:
Theo: 1090.73 [M+1]$^+$
Found: 1090.62

γ-AA-PEPTIDE STAT3/DNA INHIBITORS AND METHODS OF USE

CROSS REFERENCE TO RELATED APPLICATIONS

This application is a divisional of and claims priority to U.S. application Ser. No. 15/332,402, now U.S. Pat. No. 10,000,531, entitled "γ-AA-peptide STAT3/DNA Inhibitors and Methods of Use", filed Oct. 24, 2016, which is a continuation of and claims priority to International Patent Application No. PCT/US2015/027801, filed Apr. 27, 2015 which claims priority to U.S. Provisional Application No. 61/984,179 entitled "Identification of Novel Inhibitors that Disrupt STAT3/DNA Interaction from γ-AA-peptide OBOC Combinatorial Library", filed Apr. 25, 2014 the contents of each of which are hereby incorporated by reference into this disclosure.

STATEMENT OF GOVERNMENT SUPPORT

This invention was made with Government support under Grant No. RO1 CA140681-05 awarded by the National Institutes of Health. The Government has certain rights in the invention.

FIELD OF INVENTION

This invention relates to treatment of proliferative disorders. More specifically, the present invention provides therapeutic methods and compositions for treating cancers, such as cancers constitutively expressing STAT3.

BACKGROUND OF THE INVENTION

The Signal Transducer and Activator of Transcription 3 (STAT3) is a transcription factor that regulates many biological processes including cell proliferation, differentiation and survival (Debnath, et al., Small Molecule Inhibitors of Signal Transducer and Activator of Transcription 3 (Stat3) Protein. *Journal of Medicinal Chemistry* 2012, 55, 6645-6668; Masciocchi, et al., Signal transducer and activator of transcription 3 (STAT3): a promising target for anticancer therapy. *Future Medicinal Chemistry* 2011, 3, 567-597; Lavecchia, et al., Novel inhibitors of signal transducer and activator of transcription 3 signaling pathway: an update on the recent patent literature. *Expert Opin Ther Pat* 2014, 24, 383-400; Page, et al., Signal transducer and activator of transcription 3 inhibitors: a patent review. *Expert Opin Ther Pat* 2011, 21, 65-83). Under normal physiological conditions, the activation of STAT3 is transient and tightly regulated, and is only triggered by the stimulation of extracellular cytokines and growth factors such as IL-6, EGF and PDGF, which leads to the phosphorylation of a specific tyrosine (Y-705) on STAT3 (Sun, et al., Cucurbitacin Q: a selective STAT3 activation inhibitor with potent antitumor activity. *Oncogene* 2005, 24, 3236-3245; Turkson, et al., Novel peptidomimetic inhibitors of Stat3 signaling and oncogenesis. *European Journal of Cancer* 2002, 38, S98-S98). This phosphorylation subsequently induces the dimerization of STAT3-STAT3 which is stabilized by two reciprocal phosphotyrosine-SH2 binding interactions. The phosphorylated STAT3 dimers translocate to the cell nucleus and bind to promoter regions in DNA, resulting in regulation of specific gene expression (Zhang, et al., A Novel Inhibitor of STAT3 Homodimerization Selectively Suppresses STAT3 Activity and Malignant Transformation. *Cancer Research* 2013, 73, 1922-1933; Zhang, et al., Orally bioavailable small-molecule inhibitor of transcription factor Stat3 regresses human breast and lung cancer xenografts. *Proceedings of the National Academy of Sciences of the United States of America* 2012, 109, 9623-9628). However, STAT3 is constitutively activated in a variety of cancers including both solid tumors (i.e. breast, prostate, lung, pancreatic) and hematological cancers (i.e. lymphoma, leukemia, melanoma) (Urlam, et al., Development of new N-arylbenzamides as STAT3 dimerization inhibitors. *Medchemcomm* 2013, 4, 932-941; Siddiquee, et al., An Oxazole-Based Small-Molecule Stat3 Inhibitor Modulates Stat3 Stability and Processing and Induces Antitumor Cell Effects (vol 2, pg 787, 2007). *Acs Chemical Biology* 2009, 4, 309-309; Cheng, et al., Stat3 Inhibition Augments the Immunogenicity of B-cell Lymphoma Cells, Leading to Effective Antitumor Immunity. *Cancer Research* 2012, 72, 4440-4448). Such hyper-activation of STAT3 leads to uncontrolled cell proliferation by activating cell cycle regulators such as c-Myc and cyclin D1, and enhancement of cell survival by selectively inducing the expression of anti-apoptotic proteins including Bcl-xL and survivin. As such, STAT3 mediated signaling pathways are recognized as valid cancer targets.

Many approaches have been adopted to inhibit constitutive activation of STAT3. Among the domains of STAT3 that regulate its function are SH2 domain (dimerization domain) and the DNA-binding domain, seen in FIG. 1. Thus, STAT3 signaling can be suppressed by either inhibition of STAT3 dimerization or STAT3-DNA binding (Debnath, et al., Small Molecule Inhibitors of Signal Transducer and Activator of Transcription 3 (Stat3) Protein. *Journal of Medicinal Chemistry* 2012, 55, 6645-6668; Masciocchi, et al., Signal transducer and activator of transcription 3 (STAT3): a promising target for anticancer therapy. *Future Medicinal Chemistry* 2011, 3, 567-597; Lavecchia, et al., Novel inhibitors of signal transducer and activator of transcription 3 signaling pathway: an update on the recent patent literature. *Expert Opin Ther Pat* 2014, 24, 383-400; Page, et al., Signal transducer and activator of transcription 3 inhibitors: a patent review. *Expert Opin Ther Pat* 2011, 21, 65-83). Significant effort has been devoted to the development of STAT3/STAT3 dimerization inhibitors that disrupt the phosphotyrosine-SH2 binding (Zhang, et al., A Novel Inhibitor of STAT3 Homodimerization Selectively Suppresses STAT3 Activity and Malignant Transformation. *Cancer Research* 2013, 73, 1922-1933; Zhang, et al., Orally bioavailable small-molecule inhibitor of transcription factor Stat3 regresses human breast and lung cancer xenografts. *Proceedings of the National Academy of Sciences of the United States of America* 2012, 109, 9623-9628; Fletcher, et al., Antagonism of the Stat3-Stat3 Protein Dimer with Salicylic Acid Based Small Molecules. *Chemmedchem* 2011, 6, 1459-1470; Siddiquee, et al., An oxazole-based small-molecule Stat3 inhibitor modulates Stat3 stability and processing and induces antitumor cell effects. *Acs Chemical Biology* 2007, 2, 787-798; Gunning, et al., Targeting Protein-Protein Interactions: Suppression of Stat3 Dimerization with Rationally Designed Small-Molecule, Nonpeptidic SH2 Domain Binders. *Chembiochem* 2008, 9, 2800-2803; Mandal, et al., Synthesis of phosphatase-stable, cell-permeable peptidomimetic prodrugs that target the SH2 domain of Stat3. *Org Lett* 2009, 11, 3394-7; Mandal, et al., Potent and Selective Phosphopeptide Mimetic Prodrugs Targeted to the Src Homology 2 (SH2) Domain of Signal Transducer and Activator of Transcription 3. *Journal of Medicinal Chemistry* 2011, 54, 3549-3563; Mandal, et al., Structure-Activity Studies of Phosphopeptidomimetic Prodrugs Targeting the Src Homology 2 (SH2) Domain of Signal Transducer and Activator of Transcription 3 (Stat3). *International Journal of Peptide Research and Therapeutics* 2013, 19, 3-12). Because STAT3-DNA binding is downstream of phosphorylated STAT3 dimerization, most STAT3 dimerization inhibitors also exhibit inhibitory activity against STAT3-DNA binding (Debnath, et al., Small Molecule Inhibitors of Signal Transducer and Activator of Transcription 3 (Stat3) Protein. *Journal of Medicinal Chemistry* 2012, 55, 6645-6668; Masciocchi, et al., Signal transducer and activator of transcription 3 (STAT3): a promising target for anticancer therapy. *Future Medicinal Chemistry* 2011, 3, 567-597; Lavecchia, et al., Novel inhibitors of signal transducer and activator of transcription 3 signaling pathway: an update on the recent patent literature. *Expert Opin Ther Pat* 2014, 24, 383-400; Page, et al., Signal transducer and activator of transcription 3 inhibitors: a patent review. *Expert Opin Ther Pat* 2011, 21, 65-83). However, molecules that specifically recognize the STAT3 DNA binding domain, and therefore directly disrupt STAT3-DNA binding interactions, are rare. This is because the STAT3-DNA binding interface is large and unlike in other transcription factor/DNA interactions the STAT3 DNA binding domain is complex involving residues from multiple α-helices and β-sheets (Levy, & Darnell, Stats: transcriptional control and biological impact. *Nat Rev Mol Cell Biol* 2002, 3, 651-62). As such, the rational design of inhibitors is difficult. However, since a recent discovery suggested that phosphorylation is not required for nuclear transport of STAT3 (Nkansah, et al., Observation of unphosphorylated STAT3 core protein binding to target dsDNA by PEMSA and X-ray crystallography. *Febs Letters* 2013, 587, 833-839) and subsequent DNA binding, disruption of STAT3-DNA binding may be an alternative approach in the regulation of gene transcription compared to the inhibition of SH2 domain dimerization. Buettner, et al. (Buettner, et al., Alkylation of cysteine 468 in Stat3 defines a novel site for therapeutic development. *ACS Chem Biol* 2011, 6, 432-43) used a virtual screening to identify NSC-368262 that inhibits STAT3-DNA binding by covalently alkylating Cys468, a residue on the DNA-binding surface of STAT3.

The exploration of new and non-covalent molecular ligands that selectively inhibit STAT3-DNA binding are therefore very significant, as such an effort will not only lead to novel anti-cancer therapeutics, but also provide a new tool to further dissect the functional role of STAT3 in the regulation of cell proliferation and apoptosis. However, the art is currently underdeveloped in this field. As such, novel STATS-DNA binding inhibitors are required for therapeutic and academic use.

SUMMARY OF THE INVENTION

Based on chiral PNA backbone, a new class of peptidomimetics termed "γ-AA peptides" were recently developed, as seen in FIGS. 2 and 3 (Niu, et al., gamma-AApeptides: design, synthesis and evaluation. *New Journal of Chemistry* 2011, 35, 542-545), as they are oligomers of N-acylated-N-aminoethyl amino acids. This class of peptidomimetics can project the same number of side chains compared to a peptide of the same length (Niu, et al., Identification of gamma-AApeptides with potent and broad-spectrum antimicrobial activity. *Chem Commun (Camb)* 2011, 47, 12197-12199; Li, et al., Lipidated cyclic gamma-AApeptides display both antimicrobial and anti-inflammatory activity. *ACS Chem Biol* 2014, 9, 211-7). Additionally, they are highly amendable for the generation of chemically diverse libraries because half of their side chains can be selected from an endless set of acylating agents (Wu, et al., Rapid access to multiple classes of peptidomimetics from common γ-AA peptide building blocks. *Eur. J. Org. Chem* 2014, DOI: 10.1002/ejoc.201301841; Wu, et al., γ-AApeptide-based small-molecule ligands that disrupt Abeta aggregation. *Chemical Communications* 2014, 50; 5206-8). Moreover, they are highly resistant to proteolytic degradation (Niu, et al., gamma-AApeptides: design, synthesis and evaluation. *New Journal of Chemistry* 2011, 35, 542-545; Yang, et al., Radiolabeled gamma-AApeptides: a new class of tracers for positron emission tomography. *Chemical Communications* 2012, 48, 7850-7852). These features make γ-AA peptides a promising platform for the identification and development of potential molecular ligands and drug candidates. This has been evidenced by one-bead-one-compound (OBOC) γ-AA peptide-based combinatorial library, from which one γ-AA peptide was successfully identified that is capable of preventing the aggregation of Aβ peptides (Wu, et al., γ-AApeptide-based small-molecule ligands that disrupt Abeta aggregation. *Chemical Communications* 2014, 50; 5206-8). Thus, a similar approach of γ-AA peptide combinatorial library is assumed to be useful to identify molecular ligands that specifically disrupt STAT3/DNA interaction.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
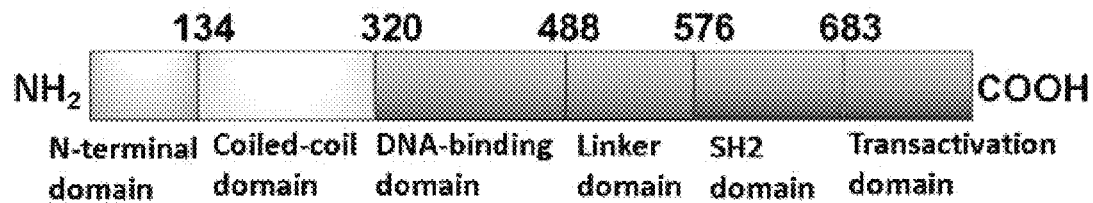
FIG. 1 is a diagram showing the domains of STAT3 protein (Levy, & Darnell, Stats: transcriptional control and biological impact. *Nat Rev Mol Cell Biol* 2002, 3, 651-62).
Figure 2:
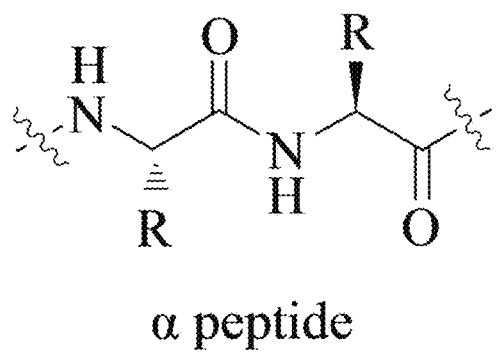
FIG. 2 is an illustration of the structure of α-amino acid peptides.
Figure 3:
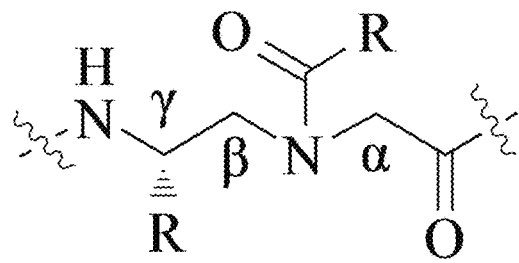
FIG. 3 is an illustration of the structure of γ-amino acid (AA) peptides.

As used herein, the singular forms "a," "an" and "the" include plural referents unless the context clearly dictates otherwise. Thus, for example, reference to "a polypeptide" includes a mixture of two or more polypeptides and the like.

As used herein, "about" means approximately or nearly and in the context of a numerical value or range set forth means±15% of the numerical.

As used herein "animal" means a multicellular, eukaryotic organism classified in the kingdom Animalia or Metazoa. The term includes, but is not limited to, mammals. Non-limiting examples include rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals.

As used herein, the term "proliferative disorders" broadly encompasses any neoplastic disease(s) including those which are potentially malignant (pre-cancerous) or malignant (cancerous) and covers the physiological condition in mammals that is typically characterized by unregulated cell growth. The term therefore encompasses the treatment of tumours. Examples of such proliferative disorders include cancers such as carcinoma, lymphoma, blastoma, sarcoma, and leukemia, as well as other cancers disclosed herein. The compositions disclosed herein are useful for treating all types of cancer, and in particular cancers which express STAT3. Cancers having constitutively expressed STAT3 include breast cancer; ovarian cancer, multiple myeloma tumor specimens, pancreatic cancer and blood malignancies, such as acute myelogenous leukemia, (Turkson, et al., U.S. Pat. No. 8,609,639; Jove, et al., WO 00/44774), multiple myeloma, acute myelogenous leukemia (Dalton, et al., PCT/US2000/001845), head and neck cancer, lung cancer, colorectal carcinoma, prostate cancer, melanoma, sarcoma, liver cancer, brain tumors, multiple myeloma, leukemia, cervical cancer, colorectal carcinoma, liver cancer, gastric cancer, prostate cancer, renal cell carcinoma, hepatocellular carcinomas, gastric cancers, and lymphomas (Li, et al., U.S. application Ser. No. 12/677,513), fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, a seminoma, an embryonal carcinoma, Wilms' tumor, testicular tumor, lung carcinoma, small cell lung carcinoma, bladder carcinoma, epithelial carcinoma, a glioma, an astrocytoma, medulloblastoma, craniopharyngioma, ependymoma, pinealoma, hemangioblastoma, acoustic neuroma, oligodendroglioma, meningioma, neuroblastoma, retinoblastoma; acute lymphocytic leukemia, acute myelocytic leukemia, chronic leukemia, and polycythemia vera (Jove, et al., U.S. application Ser. No. 10/383,707).

As used herein the term "patient" means members of the animal kingdom, including mammals, such as but not limited to, primates including humans, gorillas and monkeys; rodents, such as mice, fish, reptiles and birds. The patient may be any animal requiring therapy, treatment, or prophylaxis, or any animal suspected of requiring therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

As used herein, the term "therapeutically effective amount" refers to that amount of a therapy (e.g., a chemotherapeutic agent) sufficient to result in the amelioration of cancer or other proliferative disorders or one or more symptoms thereof, prevent advancement of cancer or other proliferative disorder, or cause regression of cancer or other proliferative disorder.

EXAMPLE

All Fmoc protected α-amino acids and Rink amide resin (0.7 mmol/g, 200-400 mesh) were purchased from Chem-Impex International, Inc. TentaGel MB NH₂ resin (0.3 mmol/g, 140-170 μm) was purchased from RaPP Polymere GmbH. Masses of γ-AA peptides were obtained on an Applied Biosystems 4700 Proteomics Analyzer. MS/MS analysis was carried out with a Thermo LTQ Orbitrap XL. Solid phase synthesis was conducted in peptide synthesis vessels on a Burrell Wrist-Action shaker. γ-AA peptides were analyzed and purified on a Waters Breeze 2 HPLC system, and then lyophilized on a Labcono lyophilizer. All cell lines were obtained from ATCC (American Type Culture Collection, Manassas, Va., USA). Human breast carcinoma MDA-MB-468 cells were maintained in Dulbecco's Modified Eagle Medium (DMEM, Life Technologies Corporation, Carlsbad, Calif.) supplemented with 10% fetal bovine serum (FBS), 10 mM sodium pyruvate, 25 mM HEPES, pH 7.5, 1000 U/ml penicillin, and 1000 μg/ml streptomycin. Primary antibodies against pY705-STAT3, Cyclin D1 and Survivin were purchased from Cell Signaling Technology (Danvers, Mass.). Primary antibodies against STATS (C-20) were purchased from Santa Cruz Biotechnology (Santa Cruz, Calif.). Primary antibody against β-actin was purchased from Sigma-Aldrich (St. Louis, Mo.).

Figure 4:
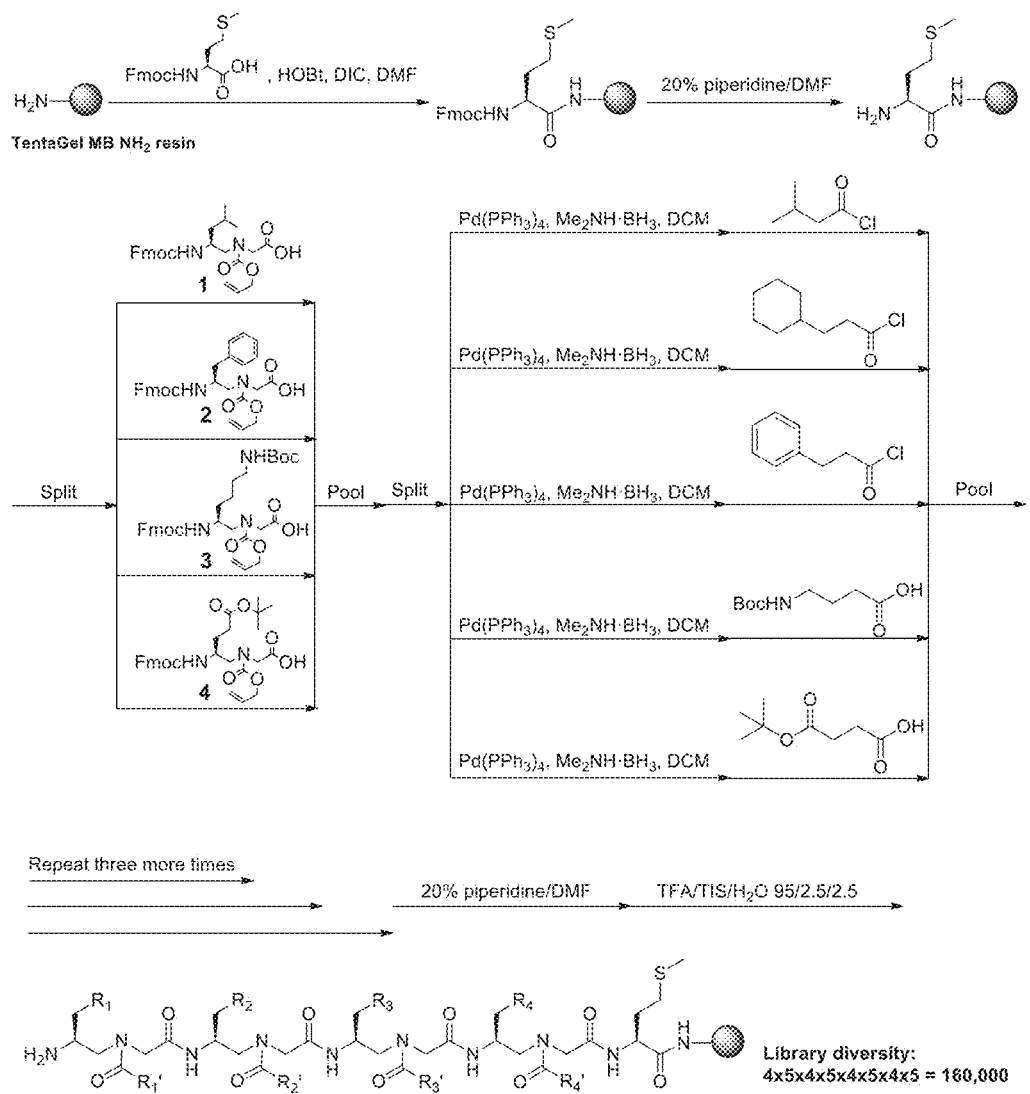
FIG. 4 is a scheme for preparation of OBOC γ-AA peptide library.
Figure 5:
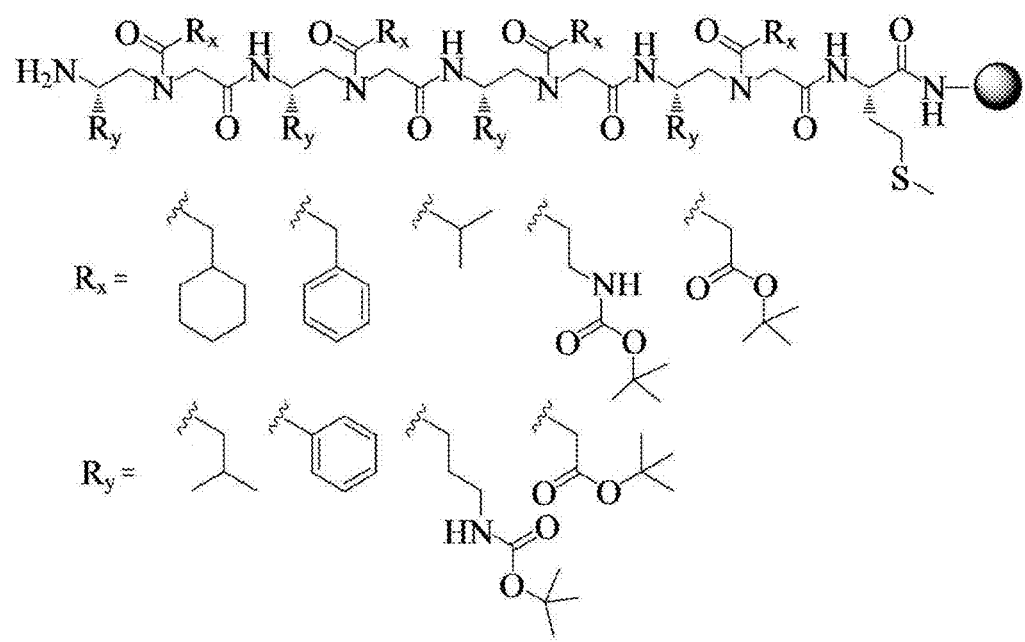
FIG. 5 is an illustration of the diversity of the library: Totally 4×5×4×5×4×5×4×6=192,000 compounds. Beads: TentaGel MB NH2, particle size: 140-170 µm, capacity: 0.5 nmol/bead.
Figure 6:
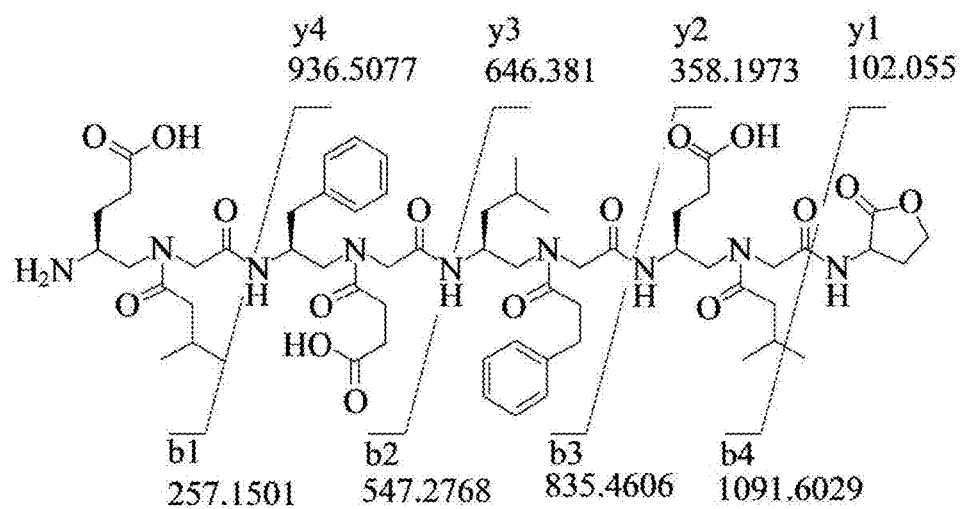
FIG. 6 is an image showing the structural identification of putative hit 1A by MS/MS analysis.
Figure 7:
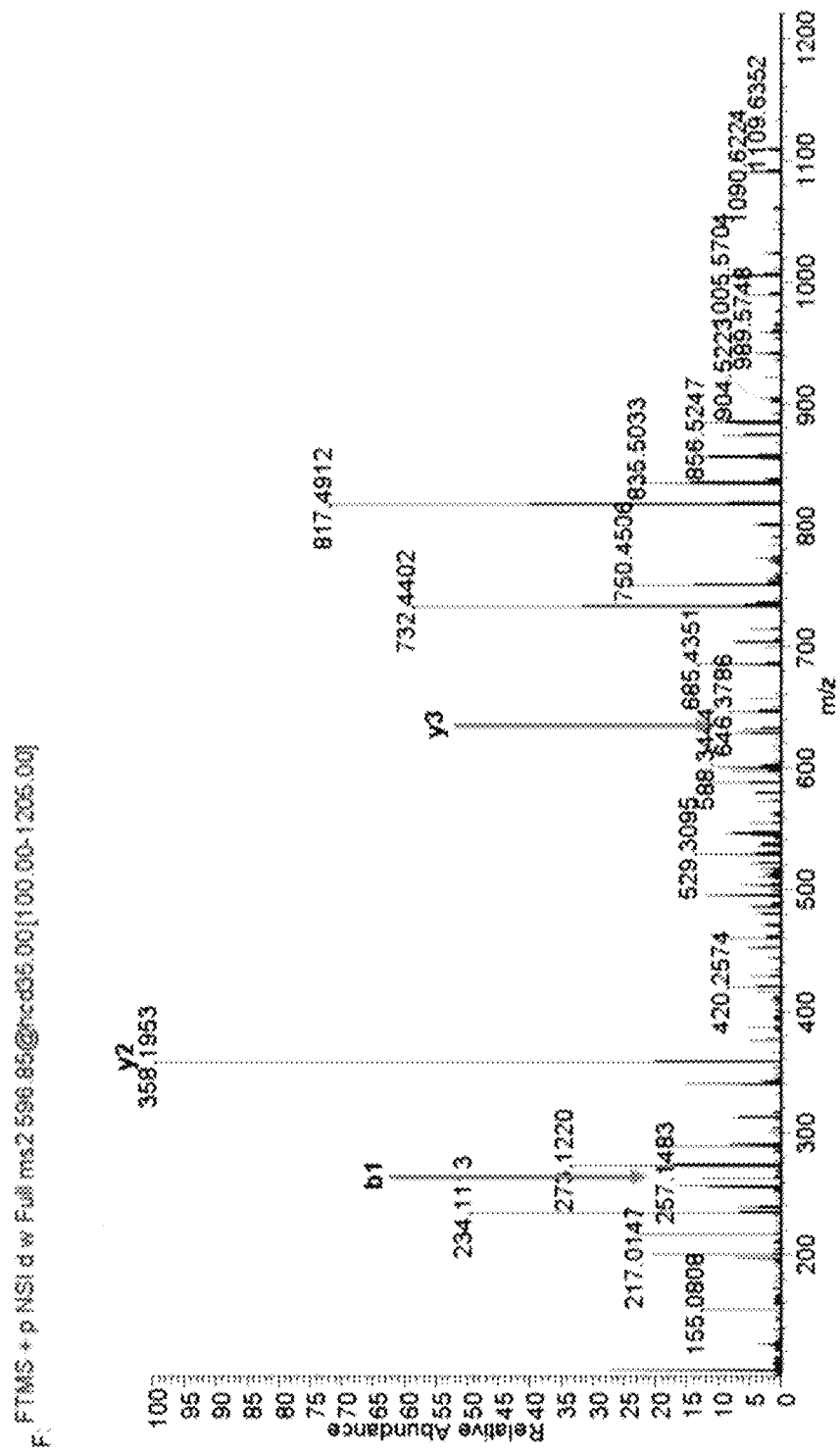
FIG. 7 is a graph showing the HCD fragmentation was performed on single or double charged precursor ions and the collision energy was set at 25 or 35 for putative hit 1A.
Figure 8:
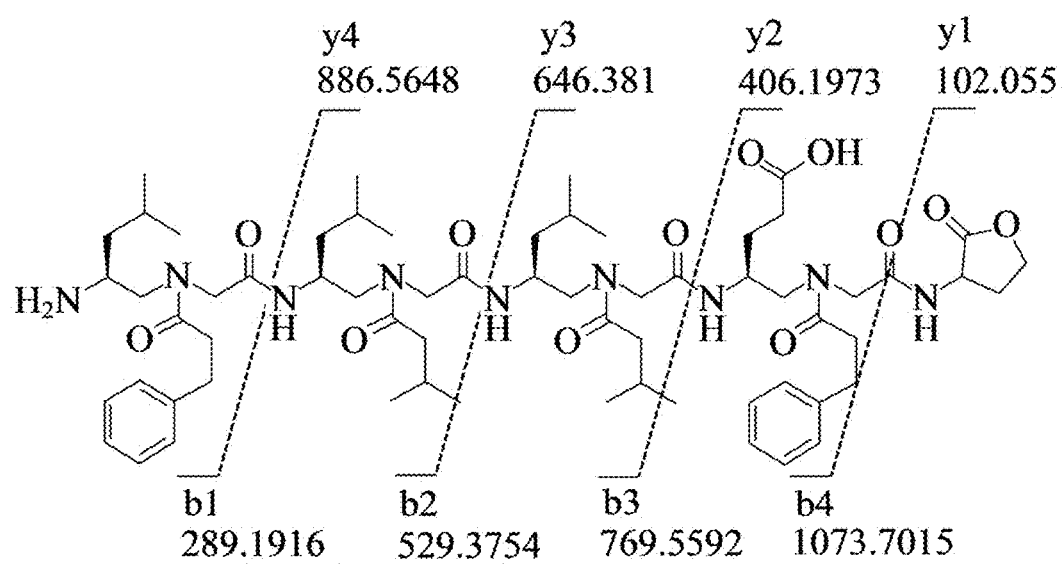
FIG. 8 is an image showing the structural identification of putative hits 2A by MS/MS analysis.
Figure 9:
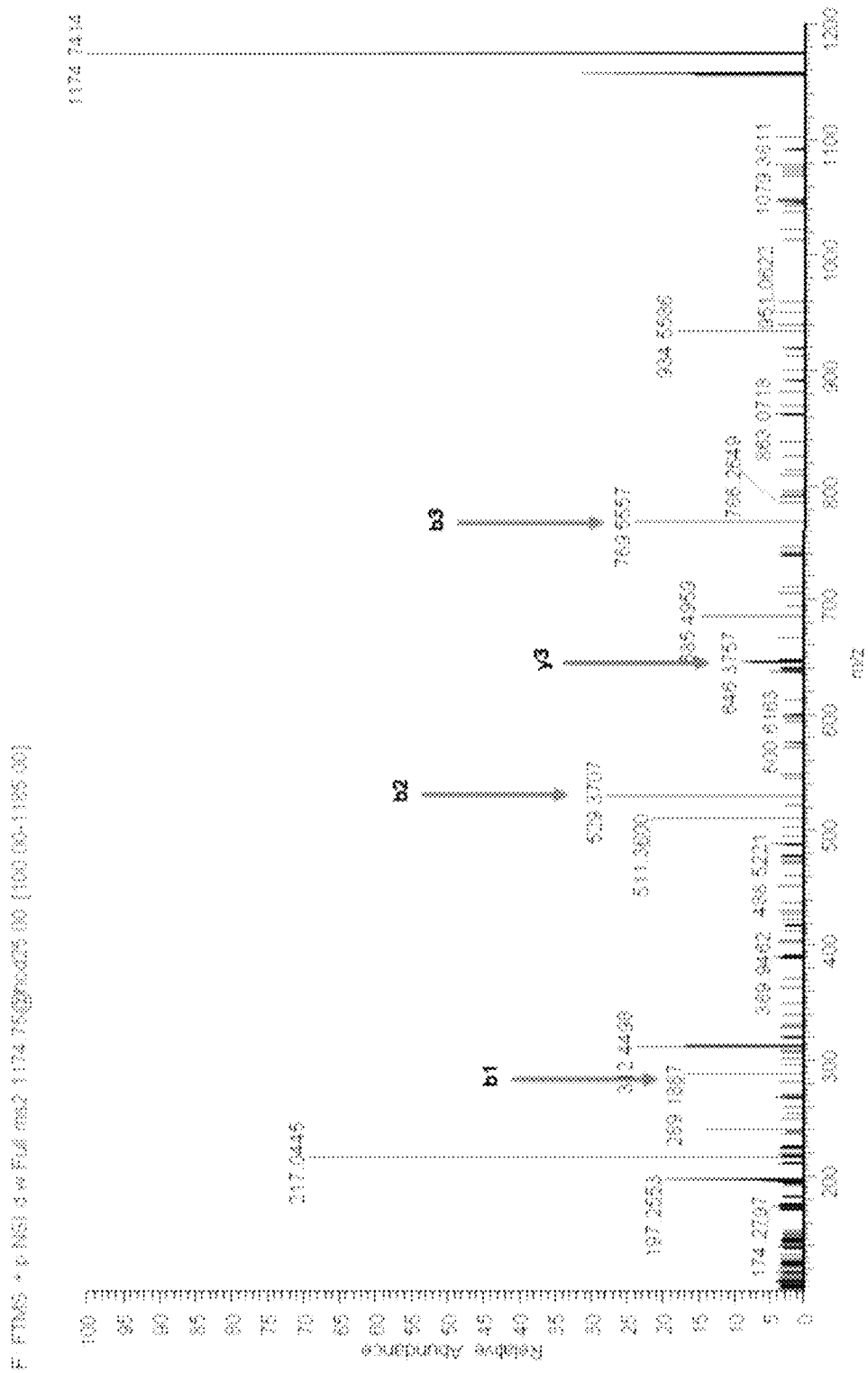
FIG. 9 is a graph showing the HCD fragmentation was performed on single or double charged precursor ions and the collision energy was set at 25 or 35 for putative hit 2A.
Figure 10:
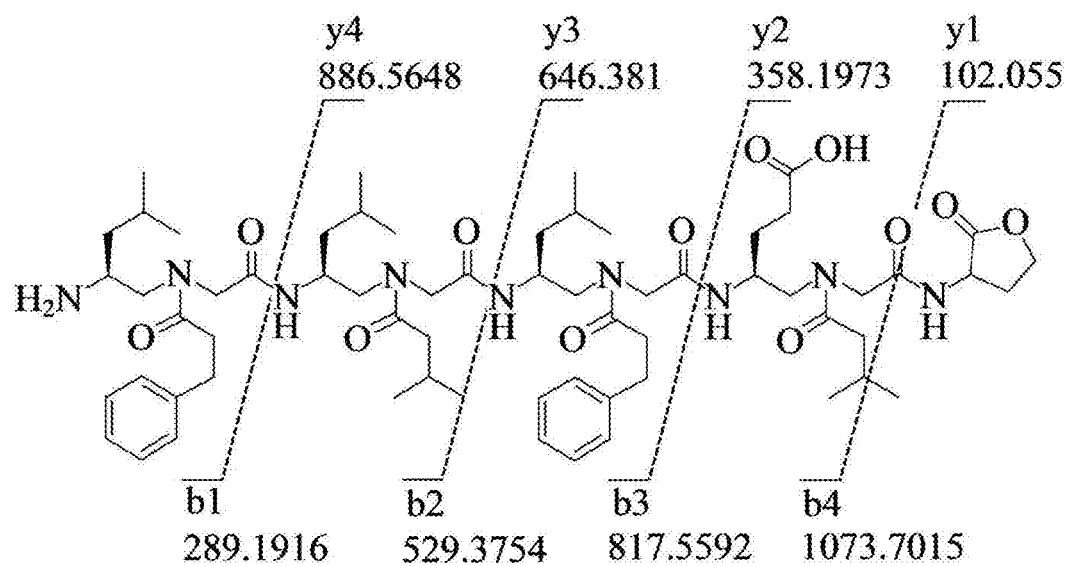
FIG. 10 is an image showing the structural identification of putative hits 3A by MS/MS analysis.
Figure 11:
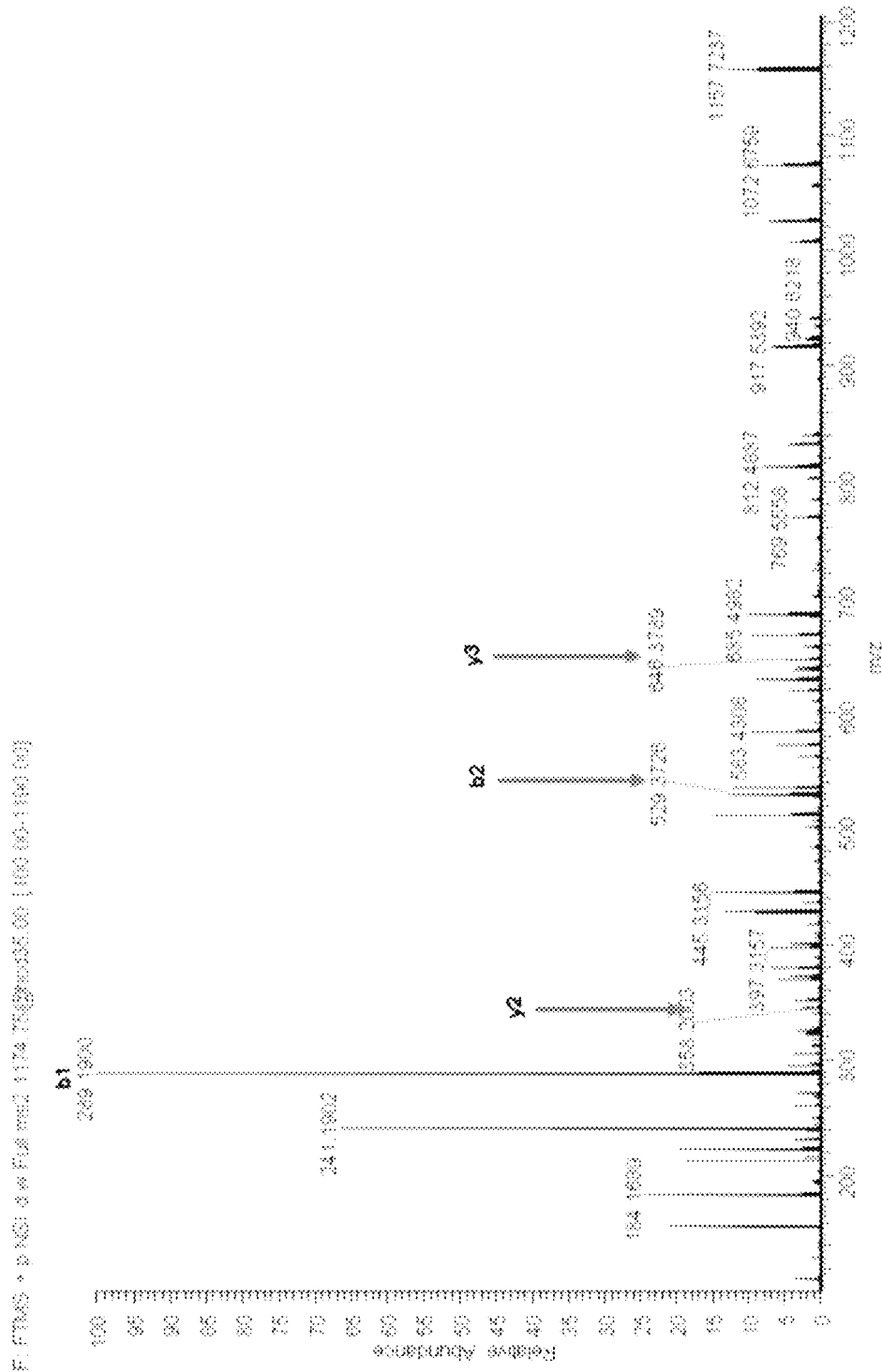
FIG. 11 is a graph showing the HCD fragmentation was performed on single or double charged precursor ions and the collision energy was set at 25 or 35 for putative hit 3A.
Figure 12:
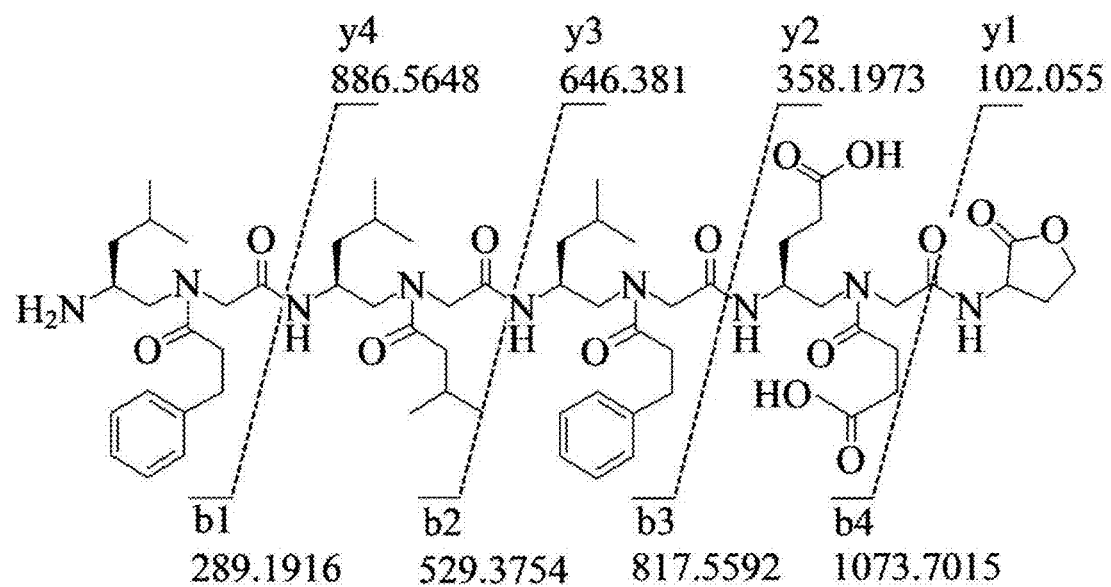
FIG. 12 is an image showing the structural identification of putative hits 4A by MS/MS analysis.
Figure 13:
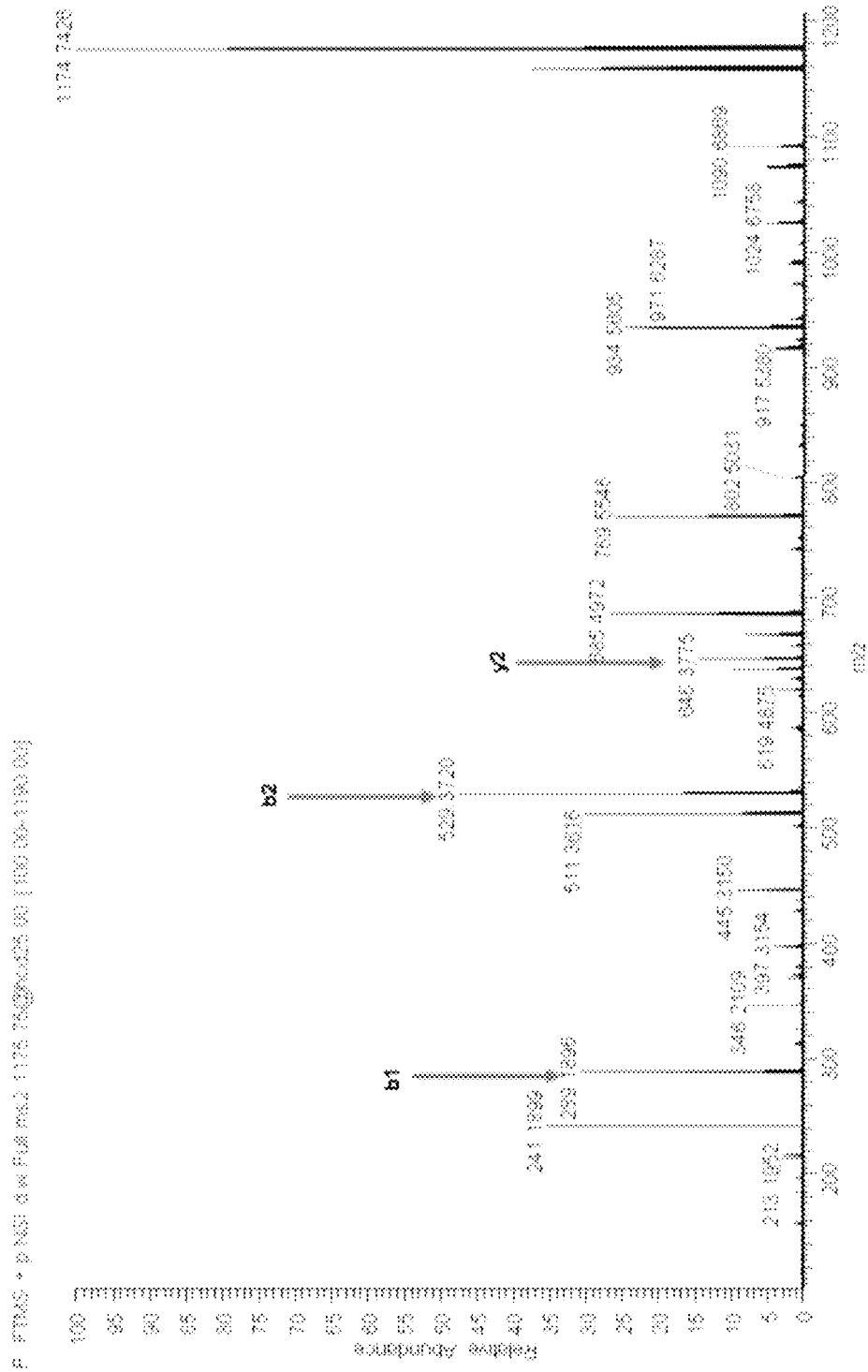
FIG. 13 is a graph showing the HCD fragmentation was performed on single or double charged precursor ions and the collision energy was set at 25 or 35 for putative hit 4A.

The OBOC γ-AA peptide library was synthesized as provided in FIG. 4 (Wu, et al., γ-AApeptide-based small-molecule ligands that disrupt Abeta aggregation. *Chemical Communications* 2014, 50; 5206-8) using four alloc-γ-AA building blocks and five acylating agents, as seen in FIG. 5, to construct the OBOC γ-AA peptide library containing 192,000 different γ-AA peptides. The sequences in the library are composed of four γ-AA peptide building blocks, which are equivalent to 8-mer peptides in length. Briefly, the TentaGel NH$_2$ resin (1.6 g, 0.48 mmol, 800,000 beads) were swelled in DMF for 1 h, then equally distributed into four peptide synthesis vessels, followed by the treatment with Fmoc-Met-OH (3 equiv.), HOBt (6 equiv.), and DIC (6 equiv.) in DMF. The beads were shaken at room temperature in a peptide synthesis vessel for 4 h, resulting in attachment of a methionine residue to the beads. The beads were washed with DCM (×3) and DMF (×3) before De-Fmoc protecting group with 20% piperidine in DMF for 10 min (×2), then washed thoroughly with DCM (×3) and DMF (×3). Each building block (2 equiv.) (Wu, et al., γ-AApeptide-based small-molecule ligands that disrupt Abeta aggregation. *Chemical Communications* 2014, 50; 5206-8) together with HOBt (4 equiv.) and DIC (4 equiv.) were dissolved in DMF, shaken for 10 min, and then added to each vessel. The coupling reaction was performed at room temperature for 4 h and repeated. The beads in each vessel were then washed, pooled together, and mixed thoroughly by vigorously shaking for 1 h. The beads were equally split into five vessels. The Alloc protecting group was removed by treating beads with Pd(PPh$_3$)$_4$ (0.1 equiv.) and Me$_2$NH.BH$_3$ (6 equiv.) in DCM for 10 min (×2). After thoroughly washing, each portion was reacted with either acid chloride or carboxylic acid. The reaction with acid chloride (5 equiv.) was carried out in the presence of DIPEA (6 equiv.) in DCM for 30 min (×2). The carboxylic acids (3 equiv.) were pre-activated with DIC (6 equiv.) and HOBt (6 equiv.) in DMF for 10 min before added to beads. The reaction was carried out by shaking the vessel for 6 hours and repeated. After that, all the beads were pooled and washed with DCM (×3) and DMF (×3) before mixed thoroughly. The previous split-and-pool process was repeated four times. At last, all beads were combined in one peptide synthesis vessel and washed thoroughly with DMF and DCM. The Met residue permitted cleavage of the γ-AApeptides from the beads upon the treatment with CNBr (Wu, et al., γ-AApeptide-based small-molecule ligands that disrupt Abeta aggregation. *Chemical Communications* 2014, 50; 5206-8; Aquino, et al., A biomimetic polyketide-inspired approach to small-molecule ligand discovery. *Nat Chem* 2012, 4, 99-104; Udugamasooriya, et al., A peptoid "antibody surrogate" that antagonizes VEGF receptor 2 activity. *J Am Chem Soc* 2008, 130, 5744-52). Beads were treated with 20% piperidine in DMF for 20 min (×2) and then with TFA/TIS/H$_2$O (95:2.5:2.5) for 2 h to remove all the protecting groups before screening or use. The beads were washed with DMF and DCM thoroughly and then dried in vacuo.

On-bead Screening of the γ-AA peptide library was performed using STAT3 as a target for the combinatorial library screen. The synthesized library compounds were stored in a peptide synthesis vessel, and then washed and incubated in the same container. The beads were screened and picked up manually under Zeiss inverted fluorescence microscope 10×43HE filter. In order to avoid any possible nonspecific binding, both the STAT3 and antibodies solution were made in 1% BSA/TBST blocking buffer.

The library synthesized on TentaGel beads (1.6 g, 800,000 beads, 160,000 compounds) as discussed previously. The beads were then swelled in DMF for 1 h, washed with 1×TBST five times and then equilibrated in 1×TBST overnight at room temperature. The beads were blocked in 1% BSA in TBST with a 1000× excess of cleared *E. coli* lysate for 1 hour, washed and equilibrated in 1×PBST before prescreening and screening.

To prescreen, the beads were incubated with mouse 1:1000 diluted STAT3 anti-mouse IgG primary antibody for 2 hours at room temperature, followed by five times 1×PBST wash and incubation with 1:1000 diluted goat anti-mouse IgG conjugated with Alexa Fluor dylight 594 for 2 hours. The beads were washed with 1×PBST completely and transferred into a 6-well plate, and the bright red beads were picked up under bench-top microscope for they had suspicious nonspecific binding. The rest of the beads were pulled together, washed with 1×PBST (5×), and then treated with 1% SDS at 90° C. for ten minutes to remove any bound proteins. Then the beads were washed with both water (5×) and 1×TBST (5×) to wash away the SDS and swelled in DMF for 1 hour. After washing (5×) and equilibrating in 1×TBST overnight, the beads were ready for actual STAT3 screening.

The prescreened beads were equilibrated in 1% BSA/PBST for 1 hour at room temperature. After washing with 1×PBST (3×), the beads were incubated with STAT3 peptide at a concentration of 20 μg/mL for 4 hours at room temperature with a 1000× excess of *E. coli* lysate. After thoroughly washing with 1×PBST, the library beads were incubated in 5 mL of 1% BSA/PBST containing 1:1000 diluted STAT3 anti-mouse IgG primary antibodies for 2 hours at room temperature. The beads were gently washed with 1×PBST (3×) and incubated with 1:1000 diluted goat anti-mouse IgG conjugated with Alexa Fluor dylight 594 for 2 hour at room temperature. The beads were washed with 1×PBST and transferred into the 6-well plate to be observed under Zeiss inverted fluorescence microscope equipped with a 10×43HE filter. Again the individual bright red beads were picked out manually using pipette tips as candidates for further study.

The putative beads were collected and washed with 1×PBST three times. The bound fluorescent dyes, proteins, and antibodies were removed by treating beads with 1% SDS solution at 90° C. for 10 min. After washing with water (3×), DMSO (3×), and acetonitrile (5×), beads were then subjected to CNBr treatment (50 mg CNBr in 1 mL 5:4:1 acetonitrile:acetic acid:H$_2$O) to cleave the compound from the beads for decoding using a previous procedure. The MALDI-MS was run on a Thermo Scientific LTQ Orbitrap XL mass spectrometer. Higher Energy Collision Dissociation (HCD) was performed at collision energy of 25 or 35 mV. HCD fragmentation of a double charged precursor ion was represented in FIGS. 6-13. Thus the structures of the unknown sequences were identified.

Figure 14:
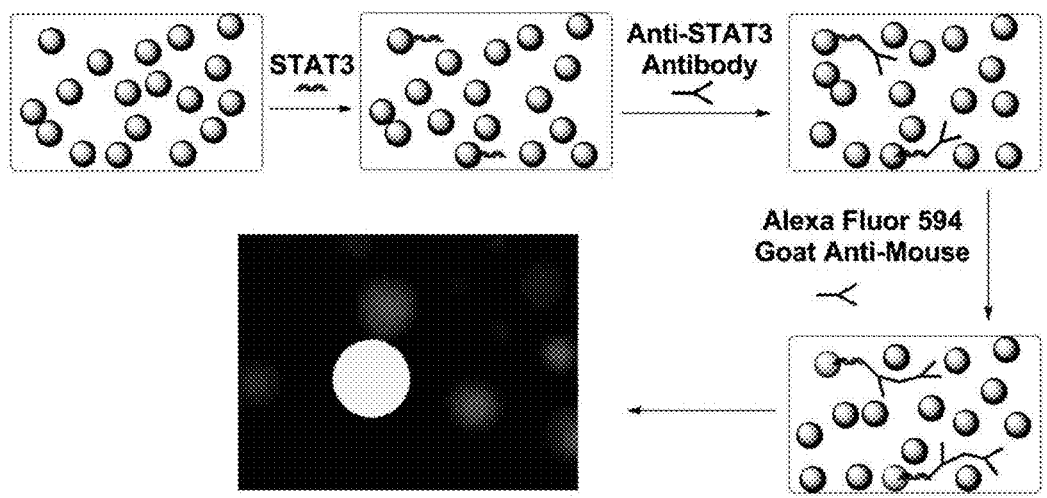
FIG. 14 is an illustration showing the scheme of OBOC screening for the identification of ligands binding to STAT3.
Figure 15:
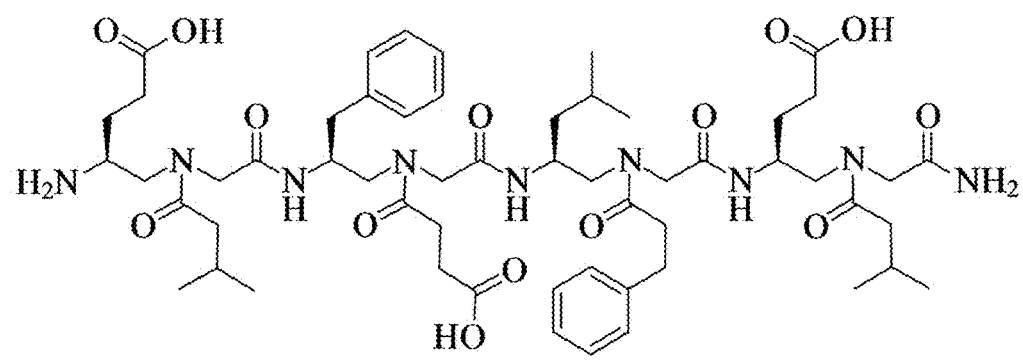
FIG. 15 is an illustration of the structures of sequence identified from γ-AA peptide OBOC library against STAT3 screening for putative hit 1.
Figure 16:
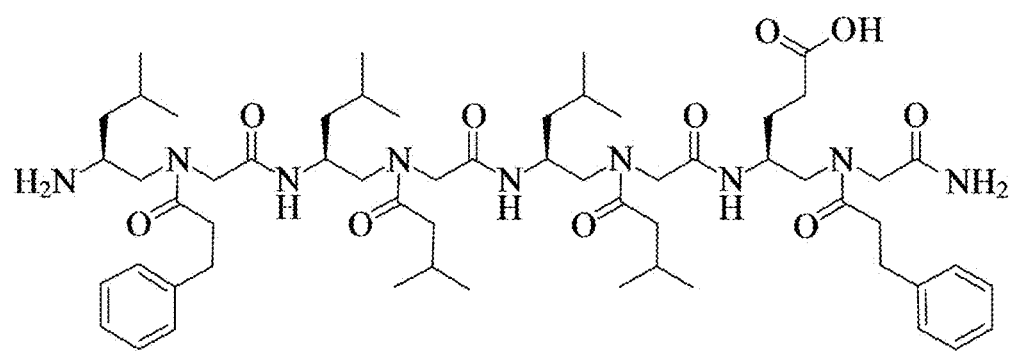
FIG. 16 is an illustration of the structures of sequence identified from γ-AA peptide OBOC library against STAT3 screening for putative hit 2.
Figure 17:
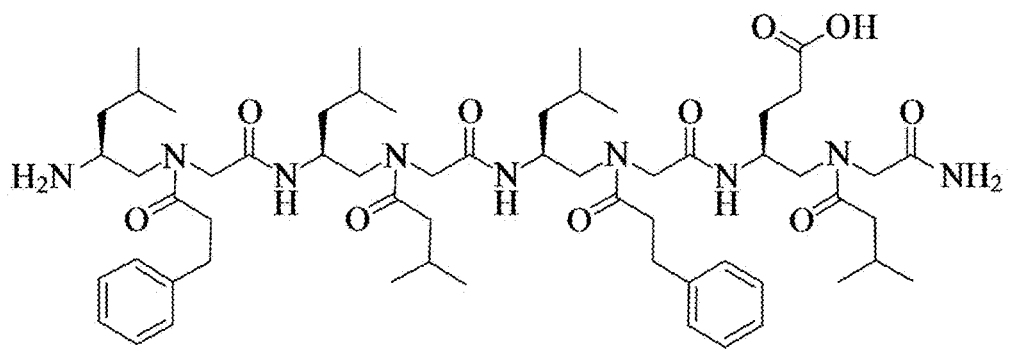
FIG. 17 is an illustration of the structures of sequence identified from γ-AA peptide OBOC library against STAT3 screening for putative hit 3.
Figure 18:
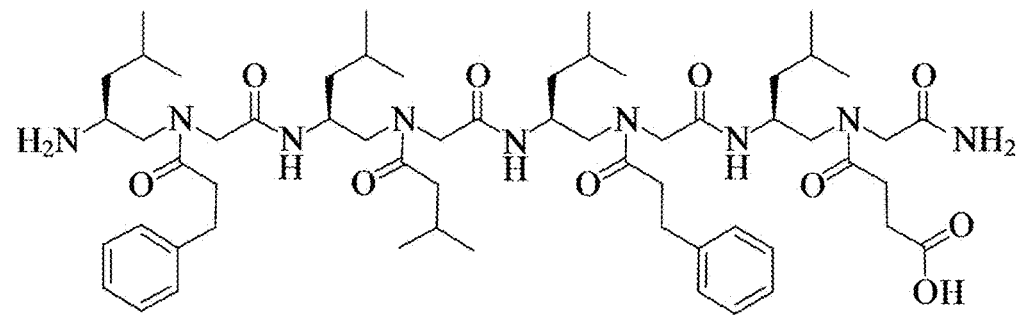
FIG. 18 is an illustration of the structures of sequence identified from γ-AA peptide OBOC library against STAT3 screening for putative hit 4.

A screening protocol was then carried out to identify ligands that potentially target STAT3-DNA binding. In brief, the library was first incubated with STAT3 (full length STAT3 protein) (please see experimental for details), followed by the incubation with anti-STAT3 antibody, as seen in FIG. 14. This antibody specifically recognizes the c-terminus of STAT3, and therefore potentially either disrupts the interaction of SH2 domain-binding beads with STAT3, or does not bind to STAT3 if such an interaction is too strong. In either case, anti-STAT3 antibody is not capable of sticking on beads recognizing SH2 domain of STAT3. Next, the library was incubated with Alexa Fluor 594 labeled secondary antibody, and the red-colored fluorescent beads were isolated by a micropipette under the microscope. Out of 192,000 beads, six positive beads were identified, suggesting the specificity of the library is high. The γ-AA peptides were cleaved off the beads by CNBr and sequenced by MS/MS (Wu, et al., γ-AApeptide-based small-molecule ligands that disrupt Abeta aggregation. *Chemical Communications* 2014, 50; 5206-8). Four sequences were identified unambiguously, and their structures are shown in FIGS. 15-18.

Figure 19:
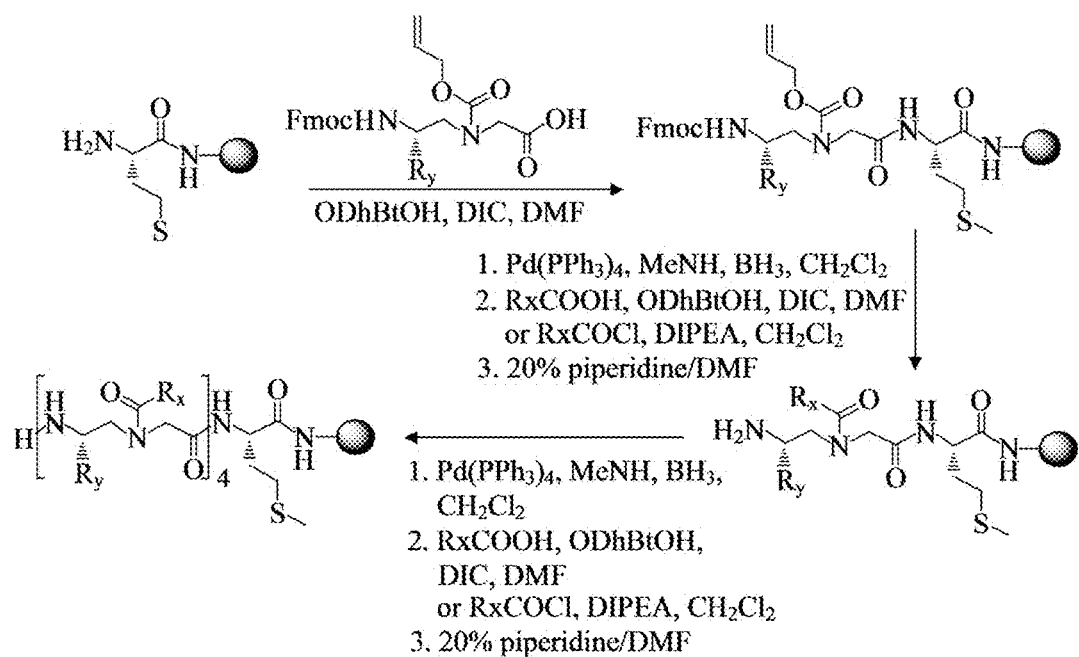
FIG. 19 is a scheme for the preparation of γ-AA peptide OBOC library. Beads: TentaGel MB NH2, particle size: 140-170 μm, capacity: 0.5 nmol/bead.
Figure 20:
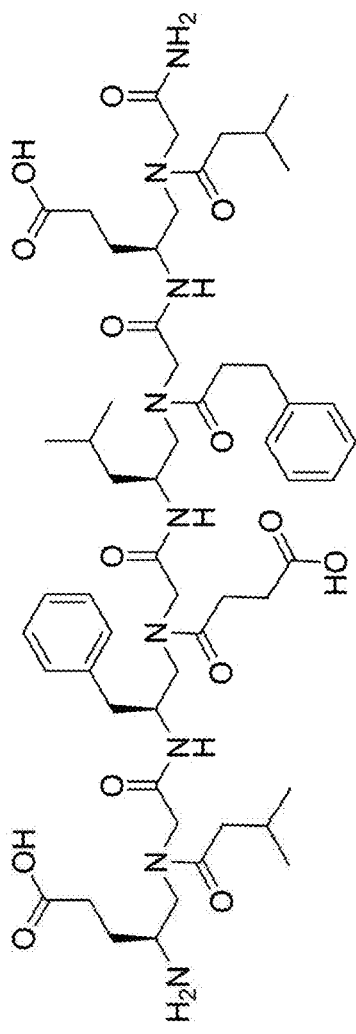
FIG. 20 are pure HPLC traces of compound 1.
Figure 20:
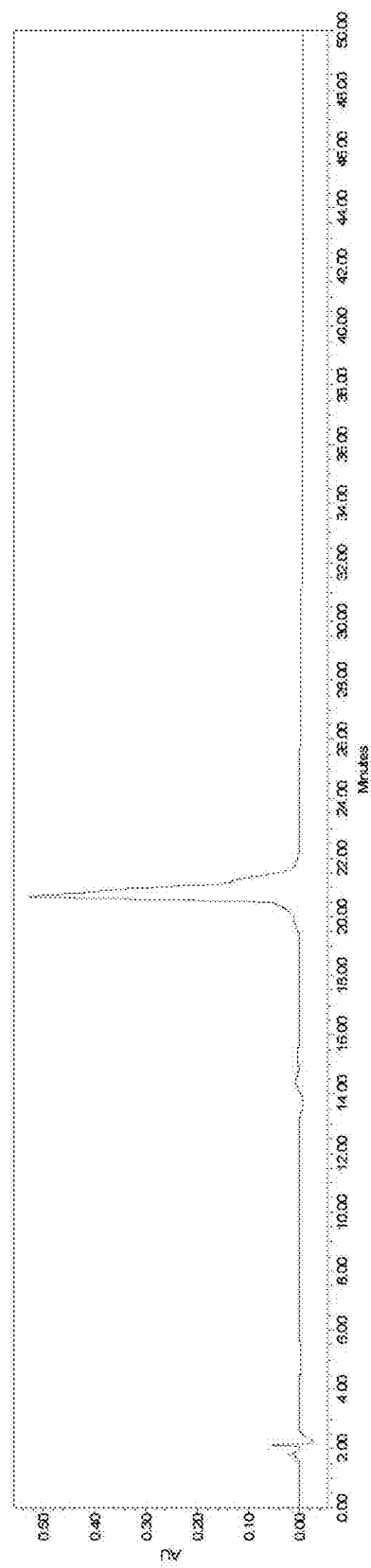
Figure 21:
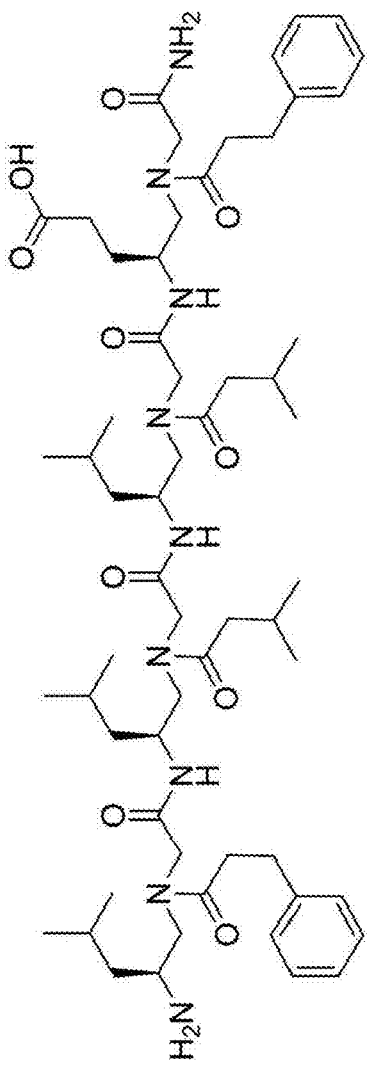
FIG. 21 are pure HPLC traces of compound 2.
Figure 21:
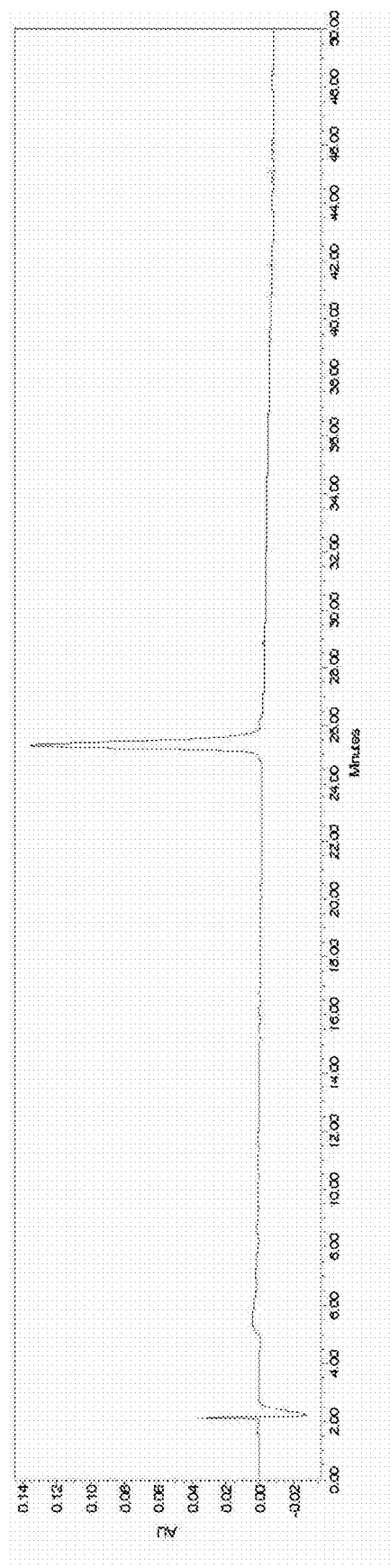
Figure 22:
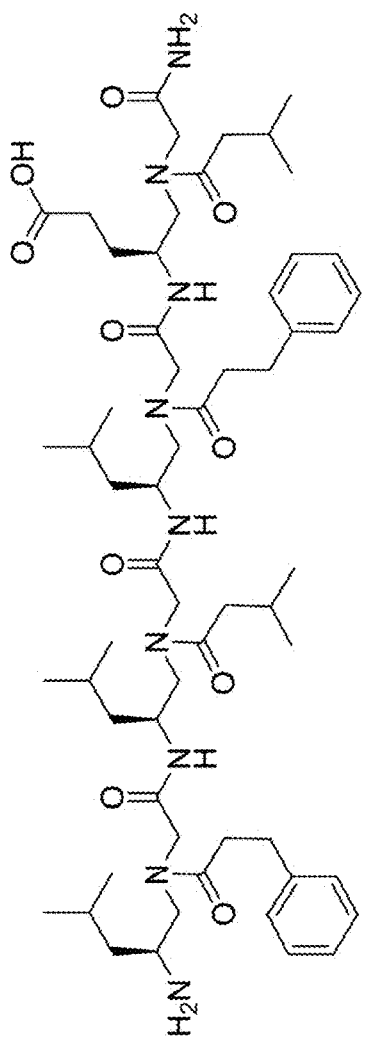
FIG. 22 are pure HPLC traces of compound 3.
Figure 22:
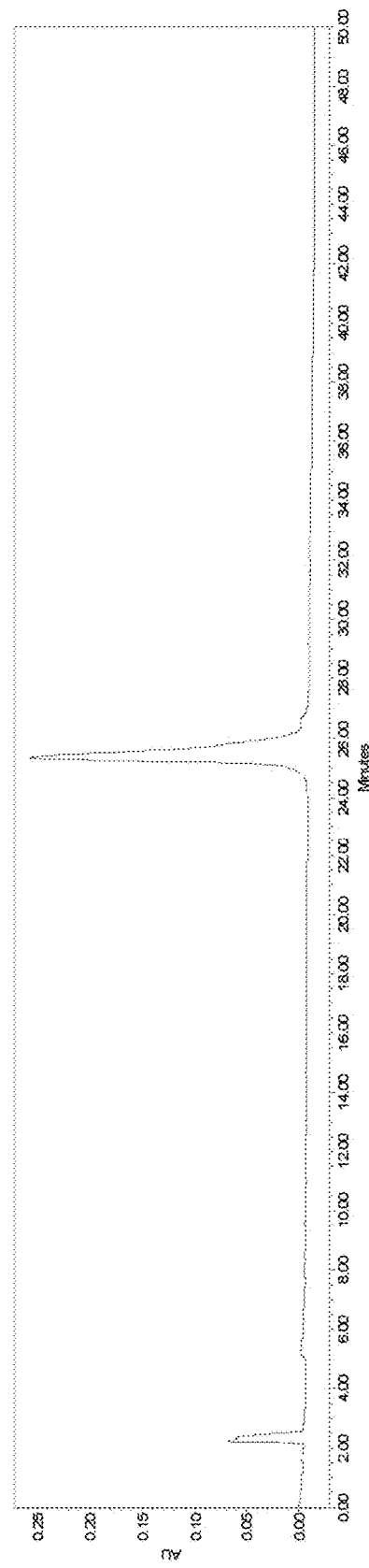
Figure 23:
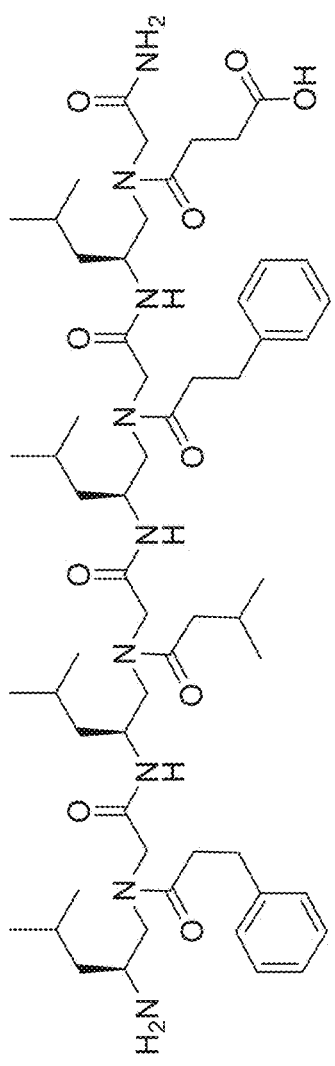
FIG. 23 are pure HPLC traces of compound 4.
Figure 23:
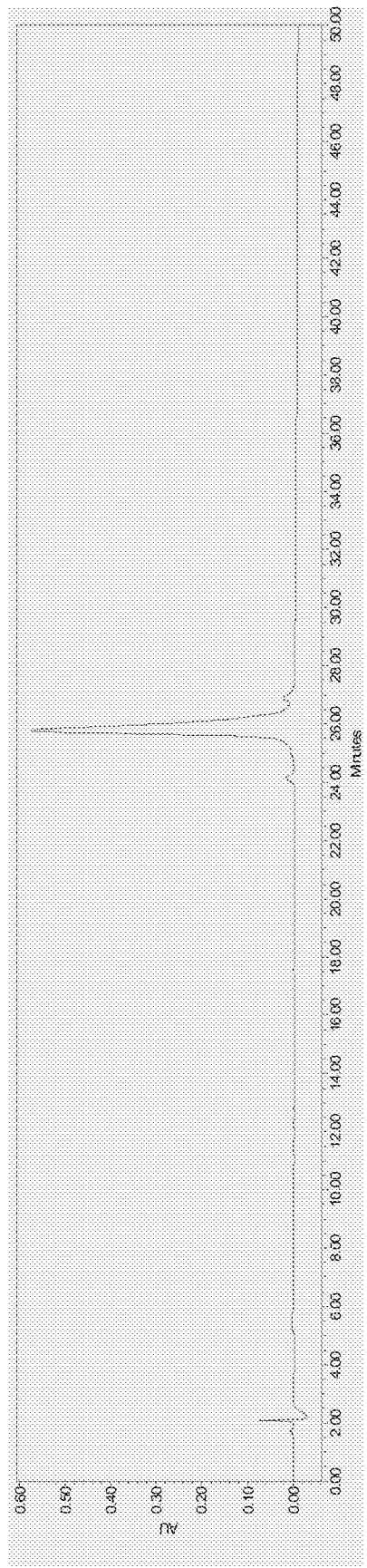

Compounds 1-4 were resynthesized on rink amide resin following a previously reported procedure, as shown in FIG. 19 (Wu, et al., γ-AApeptide-based small-molecule ligands that disrupt Abeta aggregation. *Chemical Communications* 2014, 50; 5206-8). Amino acids were assembled on rink amide resin individually using HOBt/DIC as coupling reagents. After cleavage with TFA/TIS/H$_2$O (95:2.5:2.5) for 3 h, TFA was removed under reduced pressure. The peptide was purified and analyzed on a preparative and analytical Waters HPLC system, respectively. The purity was confirmed on an analytical Waters HPLC system with flow rate of 1.0 mL/min and linear gradient from 5% to 100% (CH$_3$CN in water) in 50 min, as seen in FIGS. 20-23. Their molecular weights were identified by MALDI.

Figure 24:
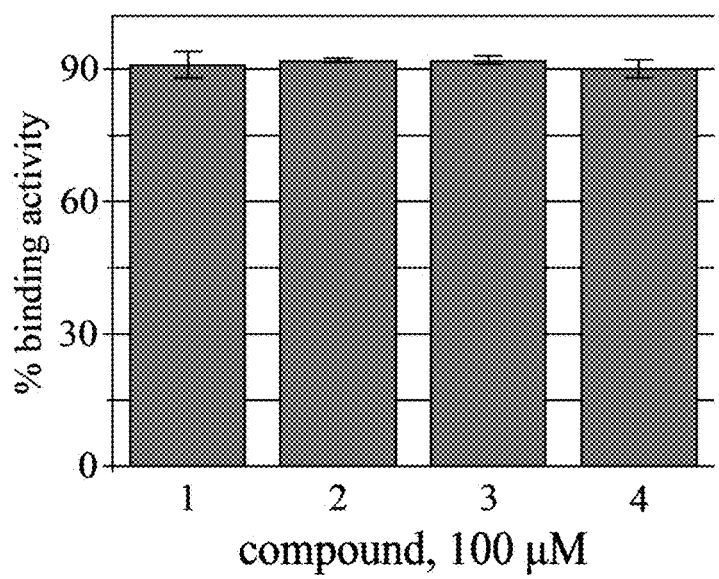
FIG. 24 is a graph showing γ-AA peptides 1-4 do not inhibit the binding of STAT3 to fluorescein-labelled GpYLPQTV (SEQ ID NO: 1) phosphotyrosine peptide by the fluorescence polarization assay.

In an effort to test the ability of the lead γ-AA peptides to inhibit STAT3-STAT3 dimerization, fluorescence polarization assays were conducted to determine whether these molecules disrupt the binding of STAT3 to fluorescein-labelled GpYLPQTV (SEQ ID NO: 1) phosphotyrosine peptide which is known to bind the STAT3-SH2 domain (Zhang, et al., A Novel Inhibitor of STAT3 Homodimerization Selectively Suppresses STAT3 Activity and Malignant Transformation. *Cancer Research* 2013, 73, 1922-1933). None of these molecules show any inhibitory activity, as seen in FIG. 24, suggesting that these γ-AA peptides do not bind to STAT3-SH2 domain, and therefore do not prevent STAT3 dimerization.

Figure 25:
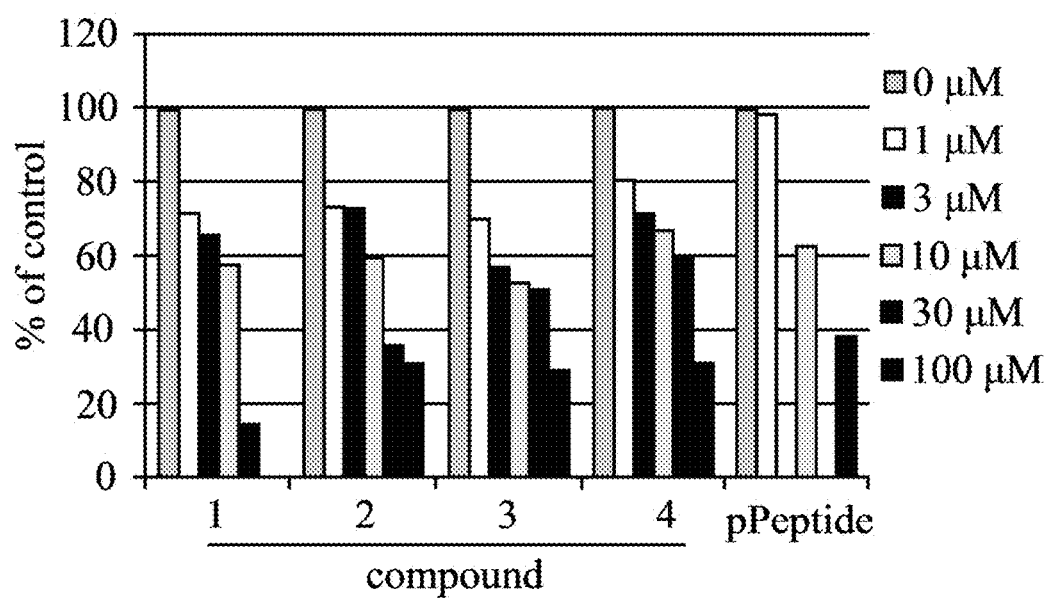
FIG. 25 is a graph showing DNA-STAT3 binding assay filter plate assay with nuclear extract from MDA-MB-468 human breast cancer cells. Compounds (0-100 μM) were added to the mixture of nuclear extract and STAT3 probe and detected by chemiluminescence.

To assess if these γ-AA peptides bind to STAT3 and therefore inhibit STAT3-DNA binding, an in vitro STAT3 filter assay was carried out, as seen in FIG. 25. Nuclear extracts from MDA-MB-468 human breast cancer cells were incubated with a biotin-conjugated STAT3 probe and tested for STAT3 DNA binding using a filter plate assay. Briefly, nuclear extract preparation was carried out as previously described (Zhang, et al., Orally bioavailable small-molecule inhibitor of transcription factor Stat3 regresses human breast and lung cancer xenografts. *Proceedings of the National Academy of Sciences of the United States of America* 2012, 109, 9623-9628). The STAT3-DNA binding filter plate assay was performed following the manual of the filter plate assay kit (Signosis, Sunnyvale, Calif.), as described previously (Zhang, et al., A Novel Inhibitor of STAT3 Homodimerization Selectively Suppresses STAT3 Activity and Malignant Transformation. *Cancer Research* 2013, 73, 1922-1933). The TF Binding buffer was mixed with the STAT3 probe (biotin labeled STAT3 DNA binding sequence) and nuclear extract and incubated at 16° C. for 30 minutes to form the STAT3-DNA complex. The STAT3-DNA complex was then separated from free probe by using a filter plate. After several steps of binding and washing, bound STAT3 probe was retained on the filter and the free DNA probe was removed. The bound pre-labeled STAT3 probe was then eluted from the filter plate by centrifugation with elution buffer. Eluted probes were then hybridized into 96-well hybridization plates for quantitative analysis. The captured STAT3 probe was detected by conjugation with streptavidin-HRP. The chemiluminescence of each well was read using 2104 EnVisionR Multilabel Reader (Perkin Elmer,) within 5 minutes after mixture with substrates. STAT3 filter DNA binding assay on intact cells is similar except the intact cells were incubated with compounds first and then nuclear lysate was incubated with STAT3 probe.

The SH2-binding phosphotyrosine peptide, GpYLPQTV (SEQ ID NO: 1), (IC$_{50}$ of 150 nM for inhibition of dimerization of STAT3-STAT3 in vitro in FP assays; Ren, et al., Identification of a high-affinity phosphopeptide inhibitor of Stat3. *Bioorganic & Medicinal Chemistry Letters* 2003, 13, 633-636) inhibited STAT3-DNA binding by 40% and 60% at 10 μM and 100 μM, respectively, in this STAT3 filter assay, as seen in FIG. 25. This is because dimerized STAT3 has higher DNA-binding affinity compared to monomeric STAT3, thus prevention of dimerization exhibits an inhibitory effect on STAT3-DNA binding. FIG. 25 also shows that all lead γ-AA peptides disrupted DNA-STAT3 binding, though the peptides did not bind to the STAT3-SH2 domain. Except for γ-AA peptide 4, the other sequences exhibited IC$_{50}$ values of 10-30 μM, with γ-AA peptide 1 inhibiting 90% of DNA-STAT3 binding at 30 μM. The fact that 1 was the most potent and 4 the least potent suggests that a negative charge was not tolerated on the N-acetylated C-terminus of the AA peptides. The negative charge is tolerated on the N-aminoethyl at the C-terminus, as well as the N-acetylated N-terminus.

Figure 26:
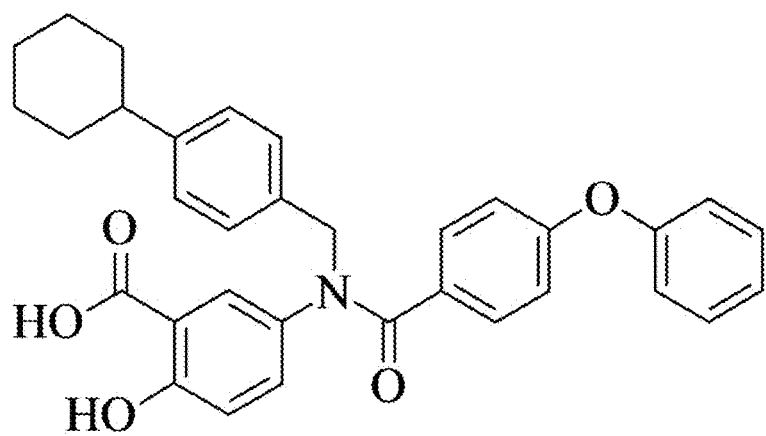
FIG. 26 is an illustration showing the structure of S3I-1757.
Figure 27:
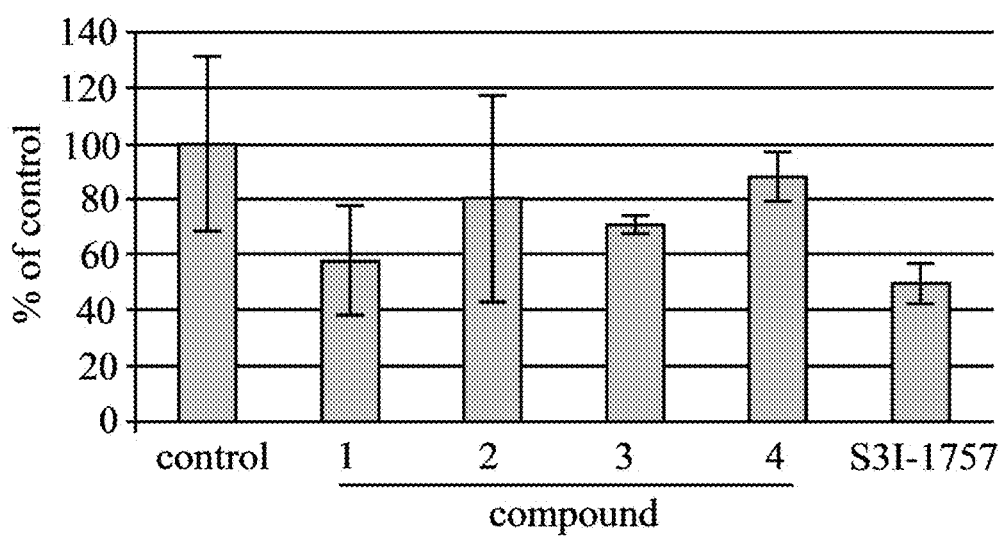
FIG. 27 is a graph showing DNA-STAT3 binding assay filter plate assay on whole cells. Intact MDA-MB-468 cells. The cells were first treated with compound then nuclear extract were prepared, and incubated with STAT3 probe and detected by chemiluminescence. S3I-1757, a previously reported inhibitor of STAT3 dimerization, is included as a control. The concentration used for all the compounds is 100 μM.

The γ-AA peptides were tested to determine if the compounds can pass through cell membranes and retain STAT3-DNA binding inhibitory activity in whole cells. As phosphotyrosine peptide GpYLPQTV (SEQ ID NO: 1) is not cell permeable, a previously reported small molecular inhibitor of STAT3 dimerization, S3I-1757, shown in FIG. 26, was included as a positive control (Zhang, et al., A Novel Inhibitor of STAT3 Homodimerization Selectively Suppresses STAT3 Activity and Malignant Transformation. *Cancer Research* 2013, 73, 1922-1933). FIG. 27 shows all γ-AA peptides were able to permeate cell membranes and disrupt STAT3-DNA binding. γ-AA peptide 1 was the most potent and its activity was comparable to S3I-1757. The results suggest γ-AA peptides are useful as molecular probes and drugs of STAT3 signaling pathways.

To assess the ability of lead γ-AA peptides to modulate the expression of STAT3 regulated genes, Western immunoblotting was carried out to determine the effect of γ-AA peptides on the expression levels of survivin and cyclin D1. Briefly, Western blots were prepared using cells that were harvested and lysed for 30 min on ice with occasional vortexing in 150 mM Hepes, pH 7.5, 150 mM NaCl, 1 mM EDTA, 0.5% NP-40, 10% glycerol, 5 mM NaF, 1 mM DTT, 1 mM PMSF, 2 mM $Na_3VO_4$, and 5 µg/ml leupeptin. Proteins readings were done using the Bradford protein assay, and equal amounts of protein for each sample were loaded into the wells of SDS-PAGE gels. After separation, proteins were transferred to nitrocellulose and Western blots were performed as previously described (Zhang, et al., A Novel Inhibitor of STAT3 Homodimerization Selectively Suppresses STAT3 Activity and Malignant Transformation. *Cancer Research* 2013, 73, 1922-1933).

Figure 28:
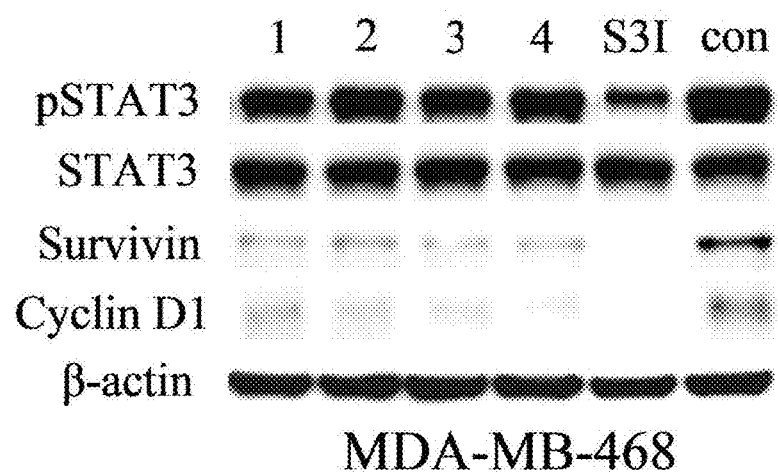
FIG. 28 is a graph showing the treatment of MDA-MB-468 cells with γ-AA peptides decreases the levels of survivin and cyclin D1 but not P-STAT3. MDA-MB-468 cells were treated overnight with 100 μM compounds and processed for Western immunoblotting with the indicated antibodies. S3I-1757 was included as positive control. The results are representative of 3 independent experiments.

Consistent with FP results, none of γ-AA peptides inhibited STAT3 phosphorylation, while S3I-1757, blocked STAT3 phosphorylation as expected as seen in FIG. 28. FIG. 28 also shows that all of γ-AA peptides decreased protein levels of survivin and cyclic D1, with similar potency to S3I-1757.

To rationalize the findings that these γ-AA peptides can disrupt STAT3/DNA binding, a computer molecular modeling was carried out by docking the most effective inhibitor 1 onto the STAT3 domain that binds DNA. The docking of the γ-AA peptide on the STAT3 DNA-binding domain was performed with Glide (Schrodinger) program. The crystal structure (PDB 1BG1) of STAT3 was used for docking. The structure was prepossessed with protein preparation wizard and then the energy minimization was applied to the structure. A box size of 20 Å×20 Å×20 Å that covers DNA STAT3 binding interface was used as the grid. The ligands were applied with a conformation search, and these conformations were used to dock the STAT3 DNA binding domain.

γ-AA peptide 1, containing multiple negatively charged carboxylate groups, is highly complementary to the STAT3 binding domain in which many cationic and polar amino acid residues are present. The three carboxylate groups interact with positively charged residues R423, R382 and K340, respectively, through electrostatic attraction, which may account for the most critical force for the binding affinity of 1 towards STAT3-DNA-binding domain. In addition, the phenyl ring near the N-terminus inserts deeply into the hydrophobic pocket formed by L430, I431 and V432. The hydrophobic interaction may further contribute to the binding specificity and affinity. Furthermore, the backbone of 1, including its C-terminus, made a few contacts with other polar and charged residues including E415, R417, N466 and Q409. Overall, the modeling suggests that the STAT3-DNA binding domain is highly positively charged. As the most negatively charged sequence in the identified γ-AA peptides, 1 binds to STAT3-DNA binding domain through a range of charge-charge interactions and hydrophobic interactions. Interestingly, the least potent γ-AA-peptide 4 has only one carboxylate that is not optimally positioned to interact with residue K340. The modeling also provides some insights into future rational design of molecules for the inhibition of STAT3-DNA binding.

An OBOC combinatorial γ-AA peptide was developed, which led to successful identification of lead compounds that disrupt STAT3-DNA interaction in nuclear extracts. The fact that these γ-AA peptides do not inhibit the binding of GpYLPQTV (SEQ ID NO: 1) to STAT3 distinguishes them from STAT3-STAT3 dimerization inhibitors (REFs). Furthermore, despite their fairly large size, the γ-AA peptides were taken up by human cancer cells, and inhibited STAT3-DNA binding and STAT3-regulated gene expression. This is not only the first report of γ-AA peptides inhibiting STAT3 function but also that γ-AA peptides are among the first few molecules that bind to STAT3 DNA-binding domain non-covalently and disrupt STAT3-DNA interaction. The results herein strongly suggest that STAT3 DNA-binding domain is a novel target for inhibiting STAT3 function, for use as novel anti-cancer agents targeting STAT3 signaling. In addition, the γ-AA peptide OBOC library can be used to identify chemical probes or drug candidates against targets traditionally believed "undruggable". Thus, with appropriate modification and further development of γ-AA peptide libraries, this strategy could be employed to develop more potent and specific ligands that bind to a variety of medicinally relevant targets.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of the invention, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

SEQUENCE LISTING

```
<160> NUMBER OF SEQ ID NOS: 1

<210> SEQ ID NO 1
<211> LENGTH: 6
<212> TYPE: PRT
<213> ORGANISM: Homo sapiens

<400> SEQUENCE: 1

Tyr Leu Pro Gln Thr Val
1               5
```

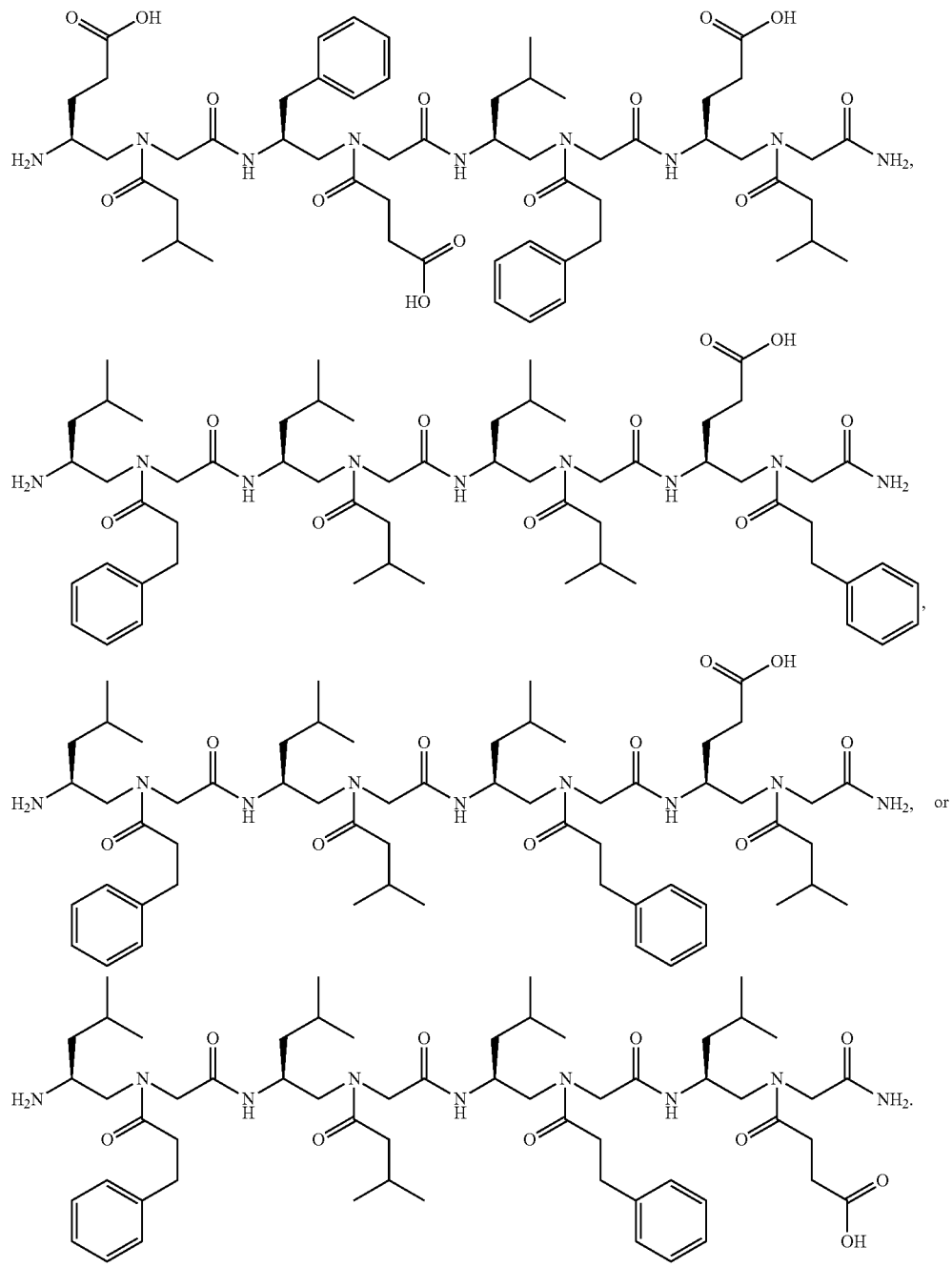

3. The method of claim 2, wherein the at least one oligomer of N-acylated-N-aminoethyl amino acids is:
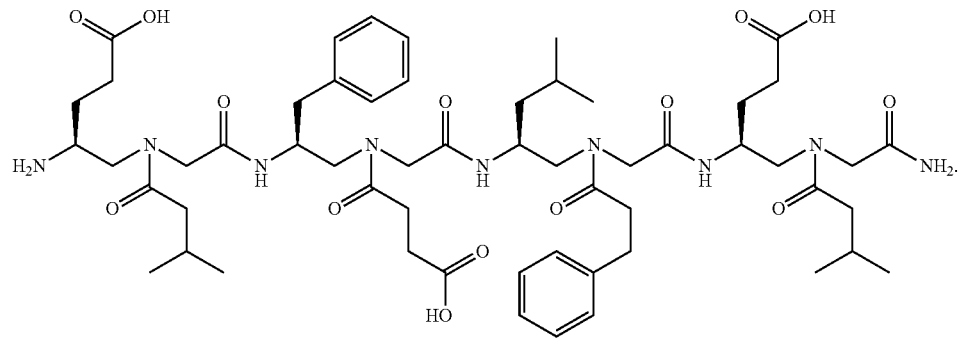 [SMILES: CC(C)CC(=O)N(CC(=O)N[C@@H](Cc1ccccc1)CN(CC(=O)N[C@@H](CC(C)C)CN(CC(=O)N[C@@H](CCC(=O)O)CN(CC(N)=O)C(=O)CC(C)C)C(=O)CCc1ccccc1)C(=O)CCC(=O)O)C[C@@H](N)CCC(=O)O]

What is claimed is:

1. A method of treating breast cancer in a patient in need thereof, comprising:
   administering a therapeutically effective amount of at least one oligomer of N-acylated-N-aminoethyl amino acids to the patient, wherein the N-acylated-N-aminoethyl amino acid has the formula:

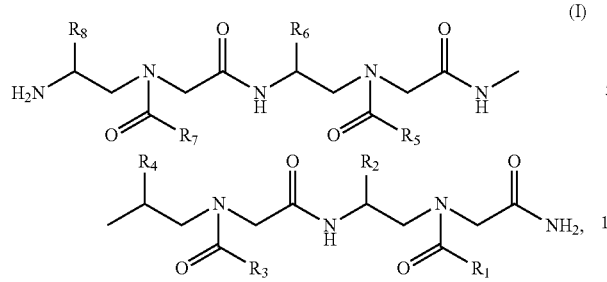

(I)

wherein $R_1$ is $CH_2CH_2(C_6H_5)$, or $CH_2(CH(CH_3)_2)$;
$R_2$ is $CH_2CH_2COOH$, or $CH_2(CH(CH_3)_2)$;
$R_3$ is $CH_2CH_2(C_6H_5)$, or $CH_2(CH(CH_3)_2)$;
$R_4$ is $CH_2CH_2COOH$;
$R_5$ is $CH_2CH_2COOH$, or $CH_2(CH(CH_3)_2)$;
$R_6$ is $CH_2CH_2(C_6H_5)$, or $CH_2(CH(CH_3)_2)$;
$R_7$ is $CH_2CH_2(C_6H_5)$, or $CH_2(CH(CH_3)_2)$; and
$R_8$ is $CH_2CH_2COOH$, or $CH_2(CH(CH_3)_2)$.

2. A method of treating breast cancer in a patient in need thereof, comprising:
administering a therapeutically effective amount of at least one oligomer of N-acylated-N-aminoethyl amino acids having the formula: